United States Patent
Bohanan et al.

(10) Patent No.: US 6,632,170 B1
(45) Date of Patent: Oct. 14, 2003

(54) ARTICULATED ARM FOR HOLDING SURGICAL INSTRUMENTS

(75) Inventors: Bryan S. Bohanan, Cincinnati, OH (US); Daniel N. Kelsch, Fairview Park, OH (US); Alexander K. Smith, Newton Falls, OH (US)

(73) Assignee: Biomec Inc., Cleveland, OH (US)

( * ) Notice: Subject to any disclaimer, the term of this patent is extended or adjusted under 35 U.S.C. 154(b) by 232 days.

(21) Appl. No.: 09/723,365

(22) Filed: Nov. 27, 2000

(51) Int. Cl.$^7$ .............................. A61B 1/00; A61B 1/32
(52) U.S. Cl. ........................ 600/102; 600/229; 403/83
(58) Field of Search ................... 600/102, 227, 600/228, 229; 403/57, 83; 248/278.1

(56) References Cited

U.S. PATENT DOCUMENTS

| | | | |
|---|---|---|---|
| 2,533,494 A | 12/1950 | Mitchell, Jr. | |
| 2,608,192 A | 8/1952 | Heitmeyer et al. | |
| 3,243,497 A | 3/1966 | Kendall et al. | |
| 3,638,973 A | 2/1972 | Poletti | 285/184 |
| 3,742,209 A | 6/1973 | Williams | 248/204 |
| 3,858,578 A | 1/1975 | Milo | |
| 4,606,522 A | 8/1986 | Heifetz | 248/276 |
| 4,718,151 A * | 1/1988 | LeVahn et al. | 24/535 |
| 4,807,618 A | 2/1989 | Auchinleck et al. | |
| 4,863,133 A | 9/1989 | Bonnell | 248/278 |
| 5,104,103 A | 4/1992 | Auchinleck et al. | 269/74 |
| 5,184,601 A | 2/1993 | Putman | 312/209 |
| 5,271,384 A | 12/1993 | McEwen et al. | 248/904 |
| 5,284,130 A | 2/1994 | Ratliff | 248/160 |
| 5,447,149 A | 9/1995 | Kikawada et al. | 600/229 |
| 5,540,649 A | 7/1996 | Bonnell et al. | 600/114 |
| 5,571,072 A | 11/1996 | Kronner | 600/102 |
| 5,597,146 A | 1/1997 | Putman | 248/276.1 |
| 5,609,565 A * | 3/1997 | Nakamura | 600/229 |
| 5,694,678 A | 12/1997 | Karasik | 29/721 |
| 5,704,900 A | 1/1998 | Dobrovolny et al. | 600/229 |
| 5,713,688 A * | 2/1998 | McCallum | 403/57 |
| 5,779,209 A | 7/1998 | Rello | 248/278.1 |
| 5,779,623 A | 7/1998 | Bonnell | 600/114 |
| 5,899,425 A | 5/1999 | Corey, Jr. et al. | 248/276.1 |
| 5,918,844 A | 7/1999 | Ognier | 248/276.1 |
| 5,927,815 A | 7/1999 | Nakamura et al. | 297/411.38 |

* cited by examiner

*Primary Examiner*—Cary E. O'Connor
(74) *Attorney, Agent, or Firm*—Pearne & Gordan LLP

(57) ABSTRACT

An articulated arm for holding surgical instruments, having elongated arm members; rotational joints connecting the arm members end to end, such that members are pivotable about the joints and at least one of the joints is selectively lockable by fluid pressure; and a plurality of tubes communicating fluid pressure between two adjacent joints. When two adjacent members are pivoted relative to one another, the tubes connecting a particular pair of joints remains substantially stationary with respect to the arm member connecting that pair of joints.

17 Claims, 11 Drawing Sheets

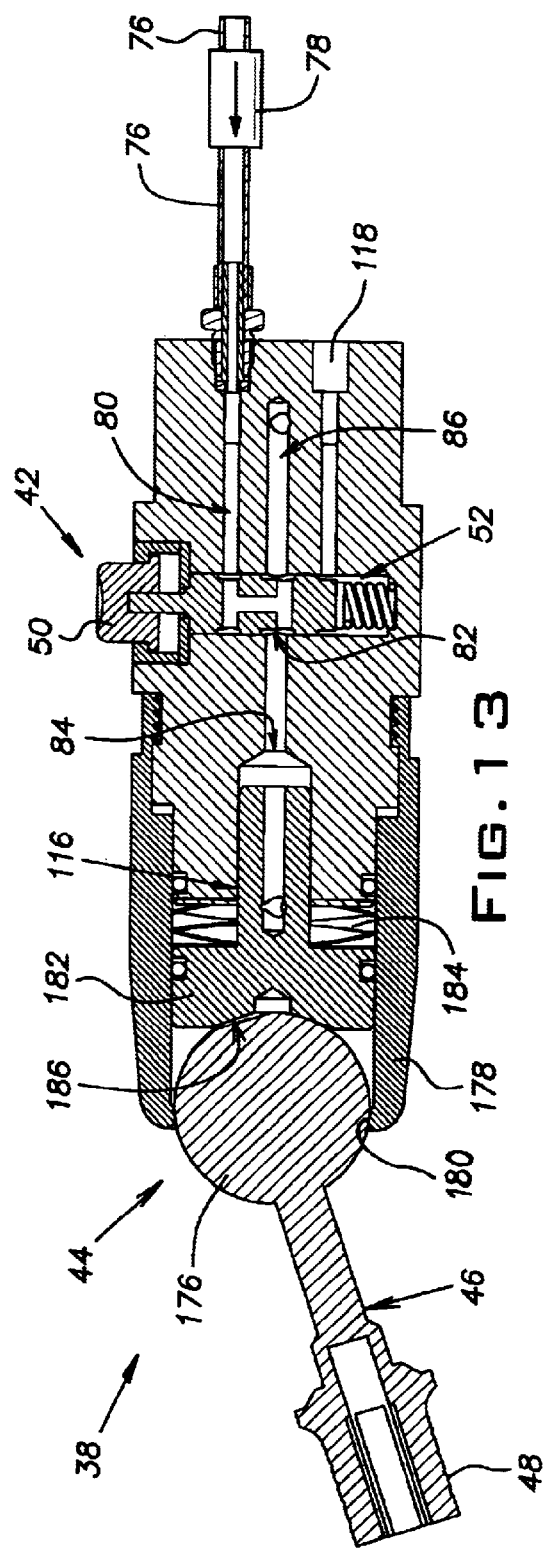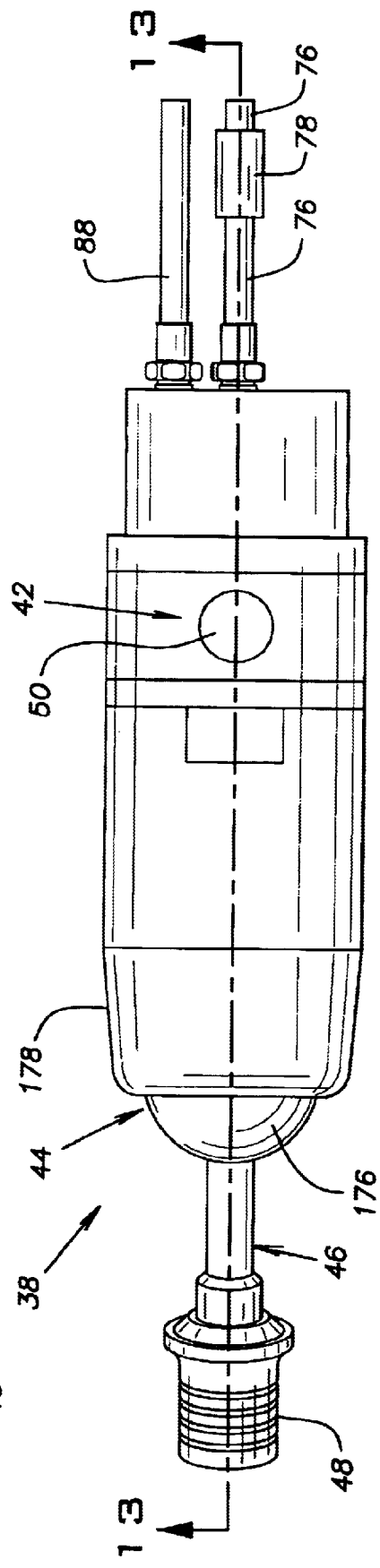

ARTICULATED ARM FOR HOLDING SURGICAL INSTRUMENTS

FIELD OF THE INVENTION

This invention relates to an articulated arm for holding a tool and more specifically for holding a medical instrument during a surgical procedure.

BACKGROUND OF THE INVENTION

In the modern practice of medicine, surgeons and other medical personnel often use endoscopic scopes, tissue retractors, and other medical instruments that must be kept steady for extended periods of time during their use on a patient. Traditionally, it may be the job of a nurse or surgical assistant to hold the instrument. However, it can be quite difficult for a person to hold the instrument steady for extended periods of time due to fatigue. Also, many of these instruments, such as tissue retractors, require great amount of force to be applied, which can rapidly lead to extreme fatigue as well as make it very difficult to keep the instrument adequately steady.

For this reason, a number of mechanical support devices have been devised to accomplish these otherwise manual tasks. One such device, as disclosed in U.S. Pat. No. 3,858,578 to Milo, consists of an arm-like structure that is made up of a series of ball and socket members held together by a cable. One end of the arm is rigidly attached to a support structure, such as an operating table rail. The opposite end supports a surgical tissue retractor. Initially, the arm is flexible and can be positioned as necessary. When the interconnecting cable is tightened by applying a fluid pressure to a piston attached at one end, the arm becomes rigid until the cable is manually released by discharging the fluid.

There are, however, many drawbacks to this and other similar prior art devices. Generally, the locking force applied to these devices is minimal, making them suitable only for very lightweight medical applications. Those devices which are capable of withstanding greater forces are generally bulky, complex and cumbersome to operate. For example, see U.S. Pat. No. 4,863,133 to Bonnell and U.S. Pat. No. 5,184,601 to Putman.

Another disadvantage that applies specifically to prior art fluid operated devices is reliability. These devices are prone to leakage, which even in a small amount can cause the locking mechanism to give out over an extended period of use. This leakage is often caused by flexible tubing which has failed due to repeated flexing. Further, if fluid pressure is lost completely during a medical procedure, the device may disengage completely, without warning, potentially causing injury to the patient. To solve this problem, some such devices have been designed to lock by default and require positive fluid pressure to unlock. While this approach provides fail-safe locking and eliminates the problem of slow leakage altogether, if fluid pressure is lost completely, a surgeon may not be able to unlock the device when needed which may also lead to the injury of the patient.

Another problem with prior art devices is their method of actuation. Most of the prior art fluid powered devices have a foot-switch which allows for hands-free operation. However, a typical modern operating room will already have several foot switches associated with various pieces of equipment. Thus, it may be exceedingly difficult for a surgeon to quickly locate the correct switch and may lead to the inadvertent release of the device. However, many hand-operated or other types of switches used in the prior art tend to be impractical, since the surgeon generally requires one or more free hands to manipulate the device and to perform other tasks.

SUMMARY OF THE INVENTION

The present invention provides an articulated arm for holding surgical instruments which comprises a plurality of elongated arm members and a plurality of rotational joints connecting said arm members end to end. The members are pivotable about the joints and at least one of the joints is selectively lockable by positive fluid pressure. A plurality of tubes communicate fluid pressure between two adjacent joints. When two adjacent members are pivoted relative to one another, the plurality of tubes located on each of the members that connect two joints remains substantially stationary with respect to the arm member connecting the pair of joints, such that it is possible for the plurality of tubes to be constructed from a rigid material.

As another aspect of the present invention, the articulated arm is provided with a fluid pressure operated friction brake for locking at least one of the joints. The friction brake includes a substantially frustoconically shaped engaging surface.

As a further aspect of the present invention, the arm is provided with a check valve that prevents inadvertent unlocking of the joints in the event that a source of fluid pressure is interrupted.

As an even further aspect of the present invention, a plurality of isolated fluid paths is provided to each joint and each of the fluid paths within each joint is isolated from the others within the joint. These fluid paths allow fluid pressure to be communicated through the joint without the need for flexible tubing.

As a still further aspect of the present invention, the articulated arm is provided with a fluid switch located near a distal end of the arm for selectively controlling the fluid pressure within at least one of the joints, thereby unlocking the joint or joints. All of the plurality of joints may be unlocked by operating the single fluid switch.

As a yet further aspect of the present invention, wherein an arm member is pivotable with respect to at least one of the joints by greater than 360 degrees.

As a yet further still aspect of the present invention, a motion-limiting mechanism is provided to at least one of the joints to prevent the inadvertent collapse of the arm.

BRIEF DESCRIPTION OF THE DRAWINGS

It should be appreciated that the depiction of the present invention in the following described drawing figures may not be shown to scale and further may be partially schematic as necessary for the purpose of illustration.

FIG. 12 is a side view of a wrist assembly of the articulated arm of FIG. 1;

FIG. 13 is a sectional view taken along a section line 13—13 shown in FIG. 12;

DETAILED DESCRIPTION OF THE INVENTION

Figure 1:
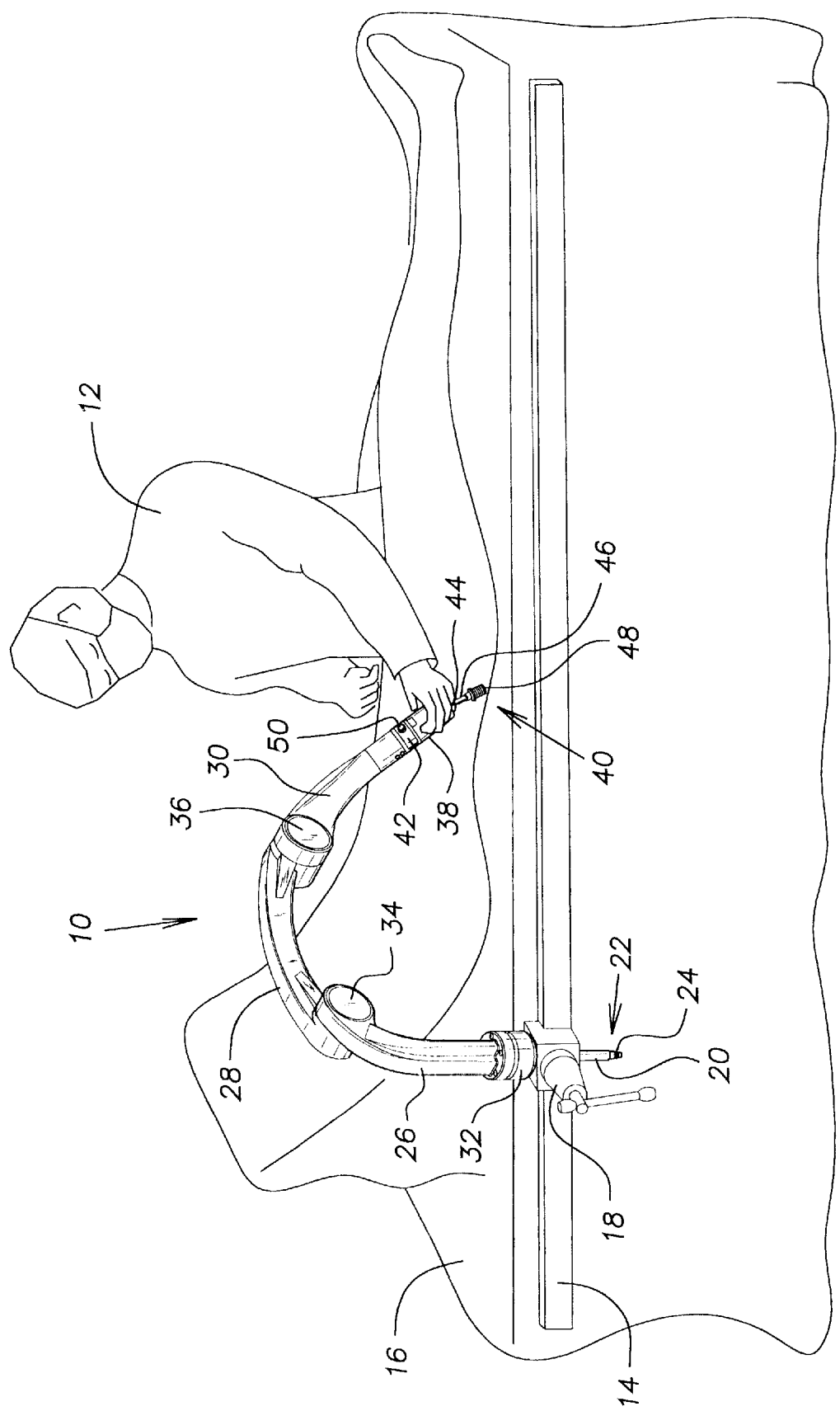
FIG. 1 is a perspective view of an articulated arm for holding surgical instruments according to the present invention shown attached to an operating table and being manipulated by a surgeon.

FIG. 1 shows an articulated arm 10 of the present invention as it might be used during a surgical procedure by a surgeon 12. The arm 10 is shown secured to a side rail 14 of a standard operating table 16 using a universal rail clamp 18. A fluid supply stem 20 is provided at a proximate end 22 of the arm 10. The stem 20 serves both to support the arm 10 in the clamp 18 and to supply the arm 10 with fluid pressure that is used as a source of power. A quick-disconnect type connector 24 is provided on the stem 20 allowing for a connection to an external source of fluid pressure (not shown). In the present embodiment, a compressed gas, such as nitrogen, carbon dioxide or compressed air, is used as the source of fluid pressure to provide power to the arm 10. A supply of such a compressed gas is readily available in most modern operating rooms, making it a convenient source of power.

Figure 2:
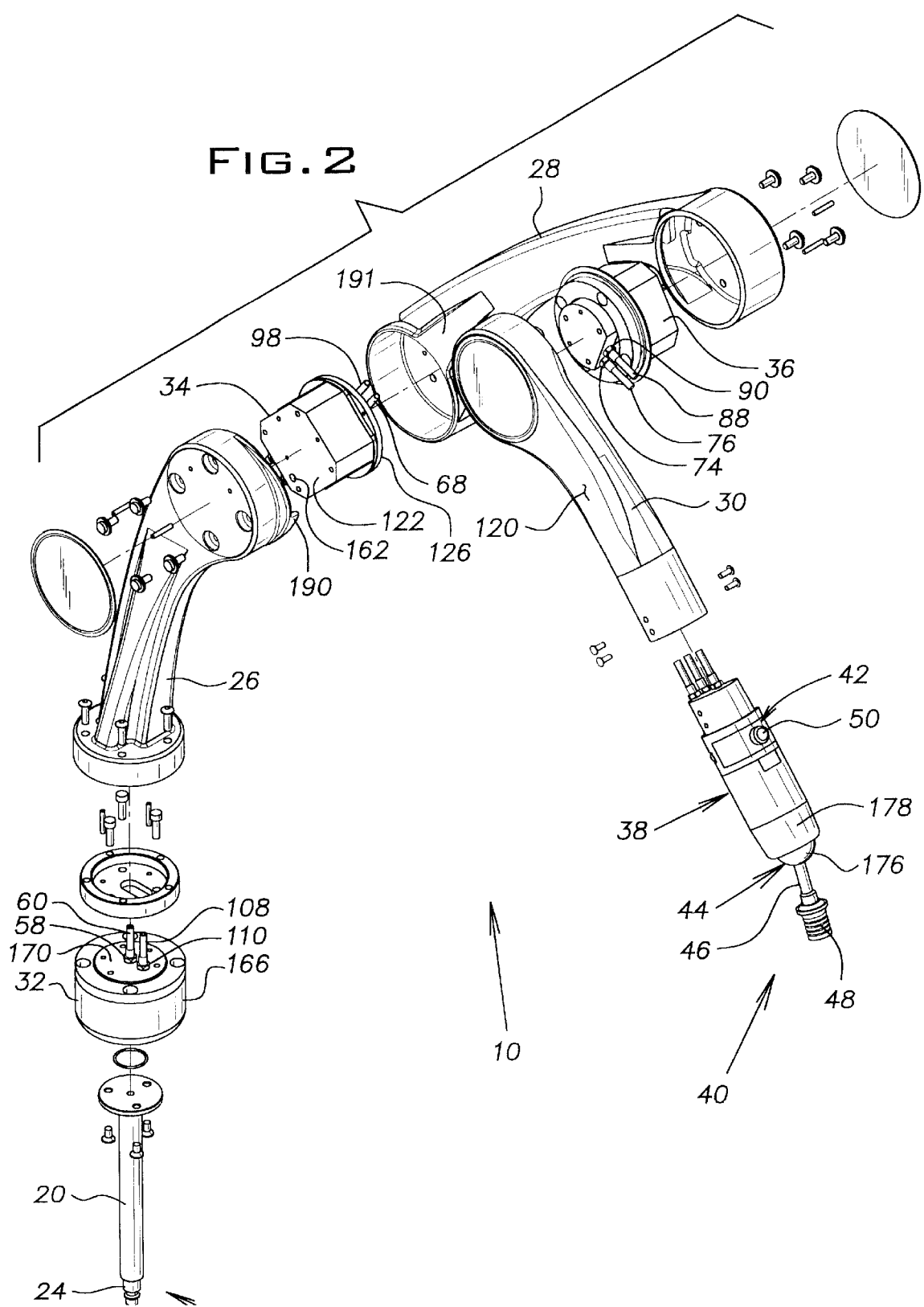
FIG. 2 is an exploded perspective view of the articulated arm of FIG. 1.

As shown in FIGS. 1 and 2, the articulated arm 10 comprises a plurality of elongated articulating arm members 26, 28, 30, including a torso 26, an upper arm 28 and a forearm 30. The arm 10 also comprises a plurality of rotational joints 32, 34, 36, including a base joint 32, a shoulder joint 34 and an elbow joint 36, which connect the arm members 26, 28, 30 to one another, end to end. As a result, the arm members 26, 28, 30 are each pivotable about the joints 32, 34, or 36 to which they are attached.

The torso 26 provides an advantage over prior art devices in that it provides a vertical offset to the shoulder joint 34. In a surgical application, such as that shown in FIG. 1, the arm 10 would normally be secured to the rail 14 of the operating table 16. The combined heights of a mattress placed on top of the table 16 and the patient's body act to raise the level of the table several inches or more beyond the rail 14 where the arm 10 is attached. The vertical offset of the shoulder joint 34 allows the arm 10 to easily clear the patient, providing for unobstructed movement of the arm 10. Further, the design of the torso 26 provides some horizontal offset to the shoulder joint 34. This horizontal offset may help the surgeon 12 to appreciate the range of movement that is available between the torso 26 and the upper arm 28 and the limits of a counter balance 188 (described in detail below), by providing directional orientation. In one sense, the offset portion of the torso 26 appears to be pointing in a direction that indicates a full extension of the upper arm 28 relative to the torso 26. The horizontal offset may also further enhance patient clearance of the arm 10 as well as adding to the overall reach of the arm 10 without increasing the structural requirements of the shoulder joint 34.

Figure 16:
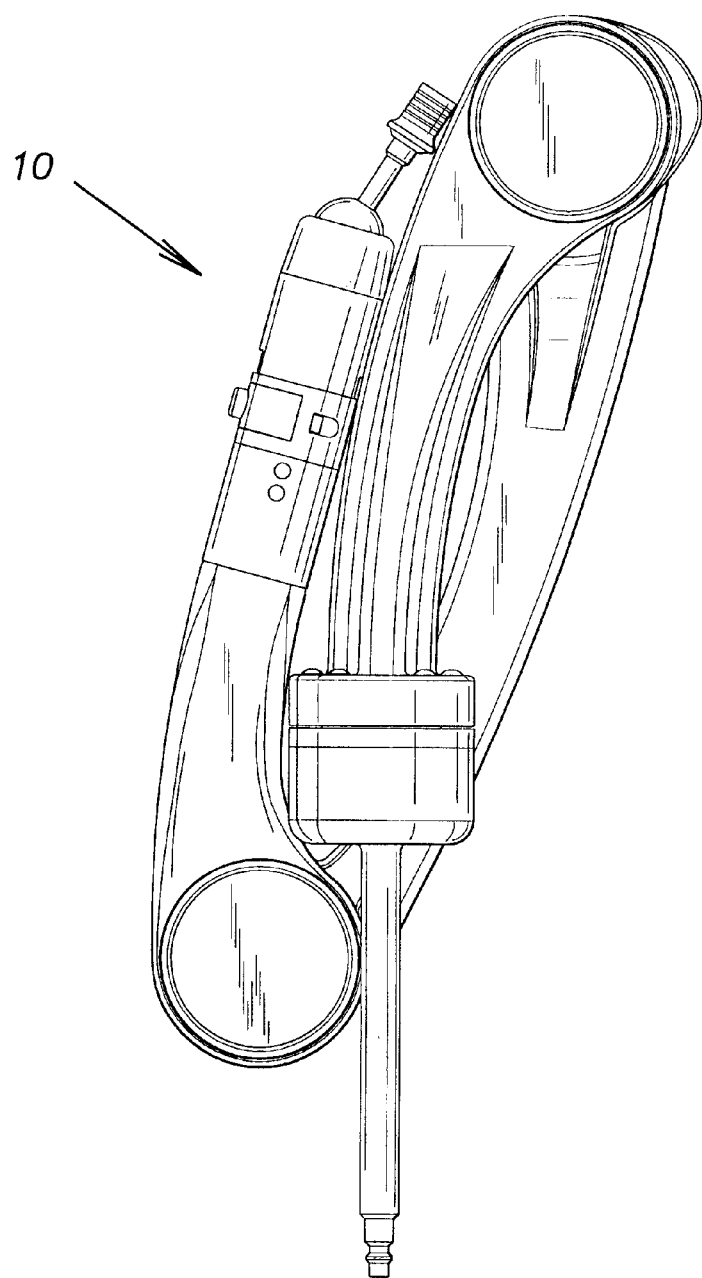
FIG. 16 is an elevation showing the articulated arm of FIG. 1 in a folded position.

As shown in FIG. 16, the arm 10 can be folded to a compact size. This may be particularly useful for storage and transportation of the arm and may also allow it to be placed into an autoclaving chamber or other sterilization equipment.

The specific relative dimensions of the arm 10 and its subcomponents as disclosed in FIGS. 1–16 are shown only by way of example. It should be appreciated that the lengths of the arm members 26–30 can be altered to meet the demands of particular applications.

All of the rotational joints 32, 34, 36 are substantially similar, and thus only the shoulder joint 34 will be described in detail. Where appropriate, any differences between the shoulder joint 34 and the other joints 32, 36 will be explained.

As shown in FIGS. 1 and 2, the arm 10 is also provided with a wrist assembly 38 at a distal end 40 of the arm 10. The wrist assembly 38 comprises a distal fluid switch 42, a ball joint 44 and an instrument stem 46.

The rotational joints 32, 34, 36 and the ball joint 44 allow the arm 10 to be selectively positioned in an infinite number of poses within a given field of range. Each joint 32, 34, 36, 44 is releasably locked in response to pressure from the external source of fluid pressure. Thus, the surgeon 12 can position the instrument stem 46 in a given location within the operating field and the arm 10 will remain locked in place, resistant to movement by external forces. The instrument stem 46 is provided with a quick-disconnect type connector 48 to allow different surgical instruments, such as a tissue retractor or an endoscope holder, to be attached.

In a typical scenario, such as that illustrated in FIG. 1, a surgical instrument is attached to the connector 48 by the surgeon 12. The surgeon then unlocks all of the joints 32, 34, 36, 44 by pressing and holding a push-button 50 provided on the distal switch 42. After positioning the instrument in a desired location and orientation by manipulating the articulated arm 10, the surgeon simply releases the push-button 50 and all of the joints 32, 34, 36, 44 are locked by the fluid pressure. The instrument may be repositioned at any time by pressing, holding and subsequently releasing the push-button 50. Since the push-button 50 is located at the distal end 40 of the arm 10, it is possible for the surgeon 12 to unlock and position the arm 10 using only one hand. This may allow the surgeon 12 to keep other hand free for tasks such as positioning or operating the surgical instrument.

As previously mentioned, the joints 32, 34, 36, 44 are locked by positive fluid pressure provided by the external fluid pressure source. Each joint 32, 34, 36, 44 is subsequently unlocked when the fluid.pressure is sufficiently reduced by the discharge of fluid. As shown in FIGS. 12 and 13, for this purpose, the distal switch 42 is provided at the distal end 40 of the arm 10. The rotational joints 32, 34, 36 are all connected as a closed-loop in series with the external fluid supply and a fluid valve 52 of the distal switch 42. The valve 52 is operated by the push-button 50 and is spring-biased to a normally open position. In this open position, the valve 52 transmits fluid pressure from the external source to the rotational joints 32, 34, 36 and also transmits fluid pressure to the ball joint 44. When the push-button 50 is pressed, the valve 52 is caused to simultaneously block the fluid pressure source and to vent all of the joints 32, 34, 36, 44 to a lower pressure environment to discharge some of the fluid. In the absence of positive fluid pressure, the joints 32, 34, 36, 44 unlock.

As will be described in detail hereafter, in the present embodiment, a series of fluid carrying tubes and passages communicate fluid pressure throughout the arm 10. The tubes primarily carry fluid between the joints 32, 34, 36, 44. The passages are provided, in part, to carry fluid from one tube, through one of the joints 32, 34, 36, 44, to another tube. As a result, the need for flexible tubing used in prior art devices that carries fluid around a joint, and is repeatedly flexed as a result of joint rotation, has been eliminated. The tubes that are provided in the present invention remain substantially stationary during operation and do not substantially interfere with the rotation of the joints 32, 34, 36.

Figure 9:
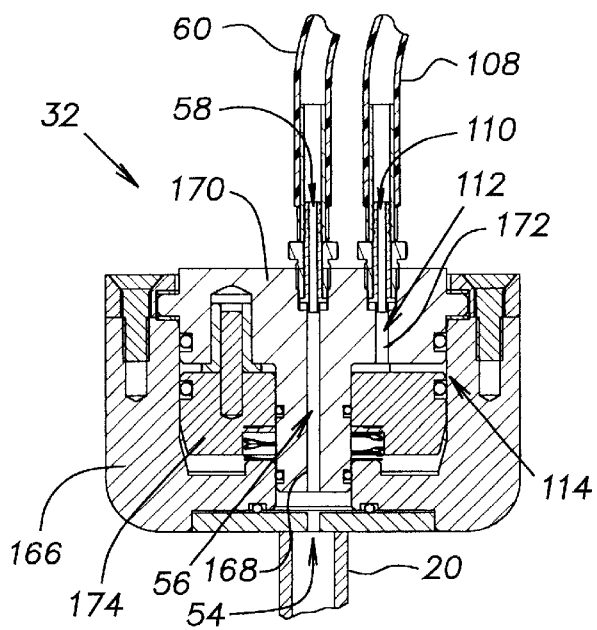
FIG. 9 is a sectional view taken along a section line 9—9 shown in FIG. 10.
Figure 11:
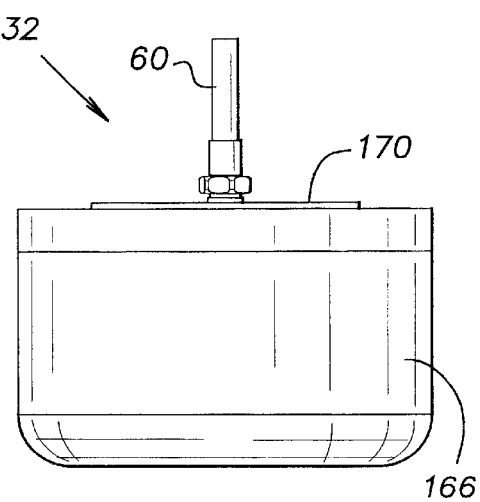
FIG. 11 is a side view of the rotary base joint of FIG. 8.

When the external source of fluid pressure is connected to the fluid supply stem 20 at the connector 24, fluid travels through the stem 20 and into a first fluid inlet 54 of the base joint 32 (see FIG. 9). A first fluid passage 56 is provided in the base joint 32 which carries the fluid to a fluid outlet 58 (see FIG. 9).

Figure 4:
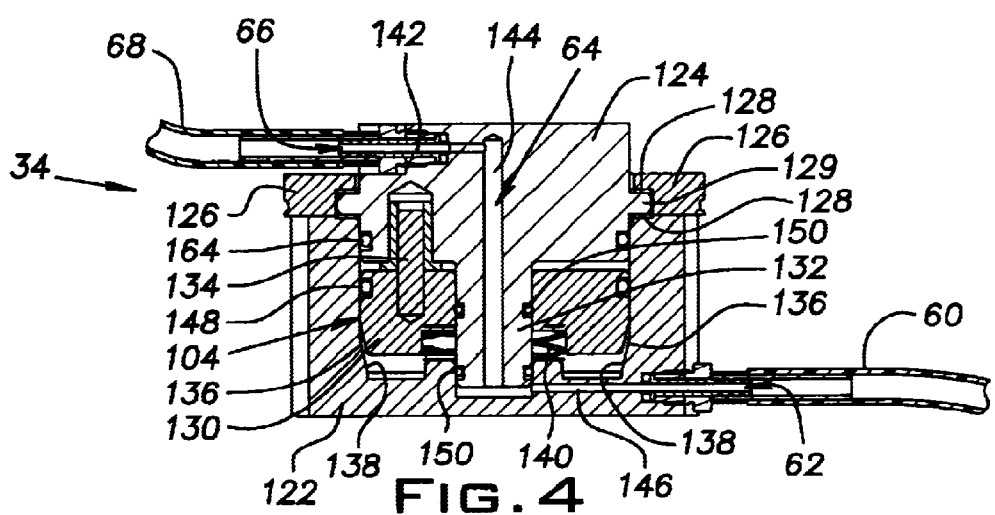
FIG. 4 is a sectional view taken along a section line 4—4 shown in FIG. 6.
Figure 7:
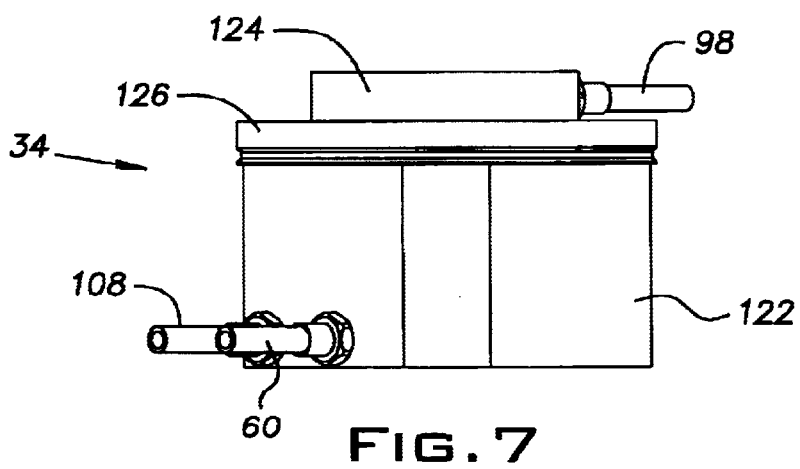
FIG. 7 is a side view of the rotary shoulder joint of FIG. 3.

The fluid then passes from the fluid outlet 58 of the base joint 32 into a first fluid supply tube 60 that extends through the torso 26 and then into a first fluid inlet 62 of the shoulder joint 34 (see FIG. 4). A first fluid passage 64 is also provided to the shoulder joint 34 which carries the fluid to a first fluid outlet 66 (see FIG. 4).

The fluid then passes from the first fluid outlet 66 of the shoulder joint 34 into a second fluid supply tube 68 that extends through the upper arm 28 and then into a first fluid inlet (not shown) of the elbow joint 36 (see FIGS. 2 and 4). A first fluid passage (not shown) provided to the elbow joint 36 carries the fluid to a first fluid outlet 74 (see FIG. 2). As noted above, details of the elbow joint 36 that are not shown are substantially the same as those of the shoulder joint 34.

The fluid then passes from the first fluid outlet 74 of the elbow joint 36 into a third fluid supply tube 76 that extends through the forearm 30, through a one-way check valve 78 (shown schematically) and then into a fluid inlet 80 of the distal switch 42 in the wrist assembly 38 (see FIGS. 12 and 13). The check valve 78 acts as a fail safe, preventing fluid pressure to the joints 32, 34, 36, 44 from being lost if the supply pressure is inadvertently interrupted. However, as will be described below, the check valve 78 is positioned directly in front of the distal switch 42, which allows the joints 32, 34, 36, 44 to be unlocked during a situation involving a loss of source pressure (see FIGS. 12 and 13). Although a particular location of the check valve 78 has been disclosed, it should be appreciated that the check valve 78 could be alternatively positioned at any point between the proximate end 22 of the arm 10 and the distal switch 42 and still function as desired.

As best shown in FIGS. 12 and 13, when the push-button 50 of the distal switch is not depressed, the valve 52 is in an open position and fluid pressure is transmitted from a first fluid outlet 82 of the distal switch 42 to a fluid inlet 84 of the ball joint 44. Also, when the valve 52 is in an open position, fluid is supplied from a second fluid outlet 86 of the distal switch 42 into a first fluid return tube 88 that extends through the forearm 30 and then into a second fluid inlet 90 of the elbow joint 36 (see FIG. 2). A second fluid passage (not shown) is provided to the elbow joint 36 which carries fluid through a friction brake assembly (not shown) and to a second fluid outlet (not shown). Fluid pressure operates the brake (not shown) which, in turn, locks the elbow joint 36, as will be explained in detail with regard the operation of the shoulder joint 34 below.

Figure 5:
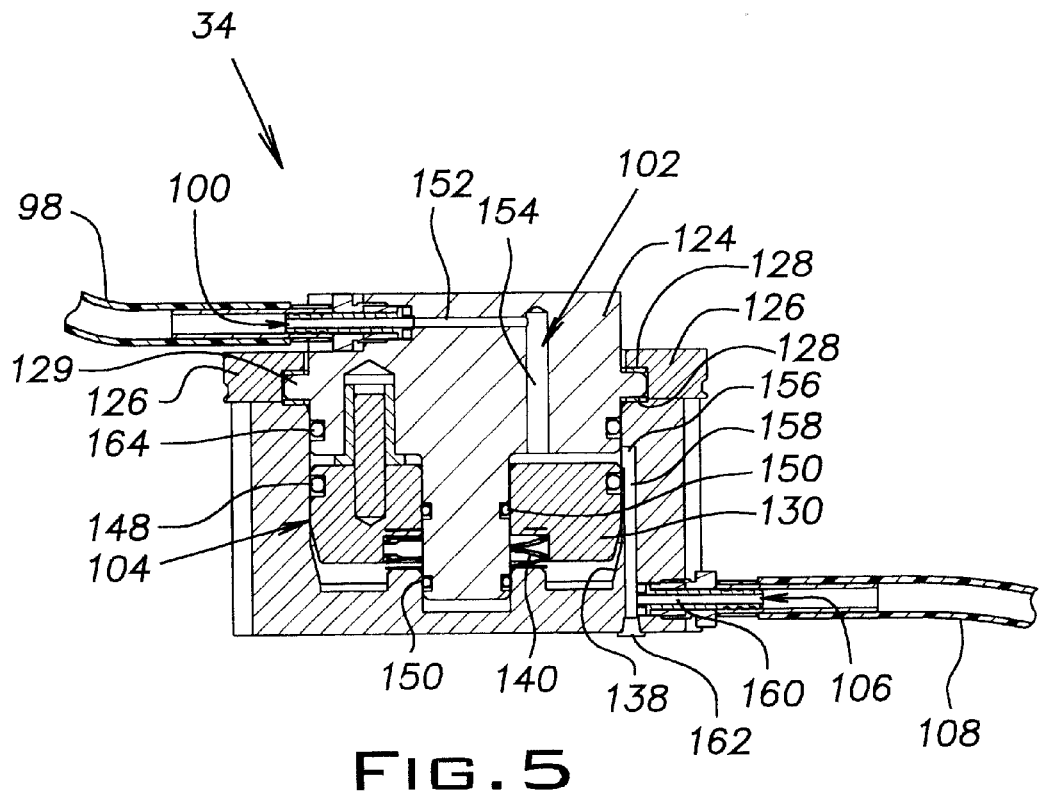
FIG. 5 is a sectional view taken along a section line 5—5 shown in FIG. 6.
Figure 8:
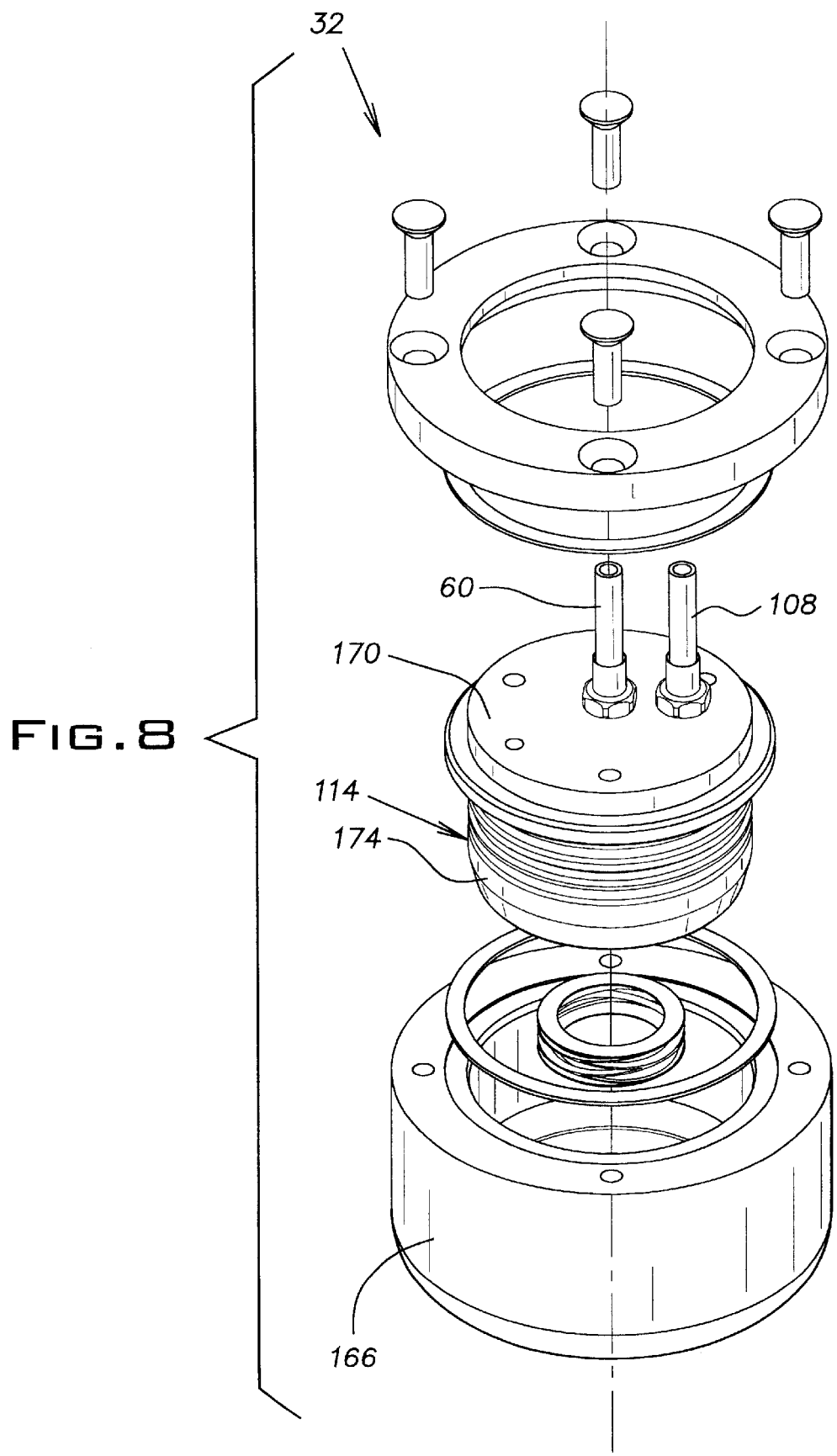
FIG. 8 is an exploded view of a rotary base joint of the articulated arm of FIG. 1.
Figure 10:
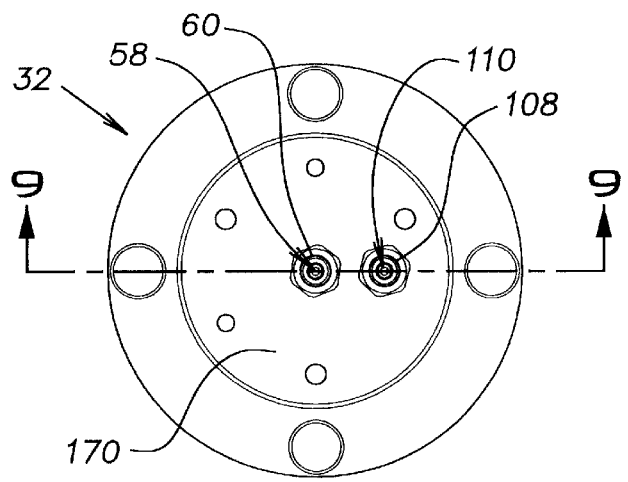
FIG. 10 is a top view of the rotary base joint of FIG. 8.

The fluid then passes from the second fluid outlet (not shown) of the elbow joint 36, and as best shown in FIG. 5, into a second fluid return tube 98 that extends through the upper arm 28 and then into a second fluid inlet 100 of the shoulder joint 34. A second fluid passage 102 is provided to the shoulder joint 34 which carries fluid through a friction brake assembly 104 and to a second fluid outlet 106. Fluid pressure operates the brake assembly 104 which, in turn, locks the shoulder joint 34, as will be explained in detail below.

The fluid then passes from the second fluid outlet 106 of the shoulder joint 34 into a third fluid return tube 108 that extends through the torso 26 and then, as best shown in FIG. 9, into a second fluid inlet 110 of the base joint 32. A second fluid passage 112 is provided to the base joint 32 which carries fluid to a friction brake assembly 114. Fluid pressure operates the brake assembly 114 which, in turn, locks the base joint 32, as will be explained in detail below.

As shown in FIG. 12 and described above, when the valve 52 is in an open position, fluid is also transmitted from the first fluid outlet 82 of the distal switch 42 to a fluid inlet 84 of the ball joint 44. This fluid is carried from the fluid inlet 84 into a friction brake assembly 116 of the ball joint 44 when operates the brake assembly 116 and, in turn, locks the ball joint 44, as will be explained in detail below.

When the push-button 50 of the distal switch 42 is depressed, causing the valve 52 to be in a closed position, the fluid inlet 80 of the distal switch 42 is blocked preventing any fluid from flowing beyond the valve 52. In this closed position, the valve 52 also connects the first fluid outlet 82 and the second fluid outlet 86 with a fluid discharge port 118. The discharge port 118 is in communication with an interior cavity 120 of the forearm 30. Thus, when the valve 52 is closed, much of the fluid in the brake assemblies 104, 114, 116 (including the brake assembly of the elbow joint 36, not shown) is discharged into the interior cavity 120 and the joints 32, 34, 36, 44 are thereby unlocked.

Since both the supplied fluid and the interior of the arm 10 may not be sterile, the fluid discharged may contain contaminants. Thus, discharging the fluid into the interior cavity 120 of the forearm 30 instead of directly into the surrounding atmosphere may help to prevent contamination of the sterile field around the operating table. As a further compliment, additional tubing establishing a third fluid path (.not shown) that is directed either around or through each of the joints 32, 34, 36 could be provided to carry the potentially contaminated fluid out of the proximate end 22 of the arm 10 and away from the sterile field of the operating table 16.

As shown in FIGS. 3–7, the shoulder joint 34 comprises a housing 122 and a face plate 124. The face plate 124 rotates freely within the housing 122 and is held in place by a retaining ring 126. The retaining ring 126 is secured to the housing 122 by four bolts 127. Two thrust washers 128, comprising TEFLON or another suitable material, are provided above and below a flange 129 of the faceplate 124 to reduce friction between the retaining ring 126, faceplate 124 and the housing 122.

Figure 3:
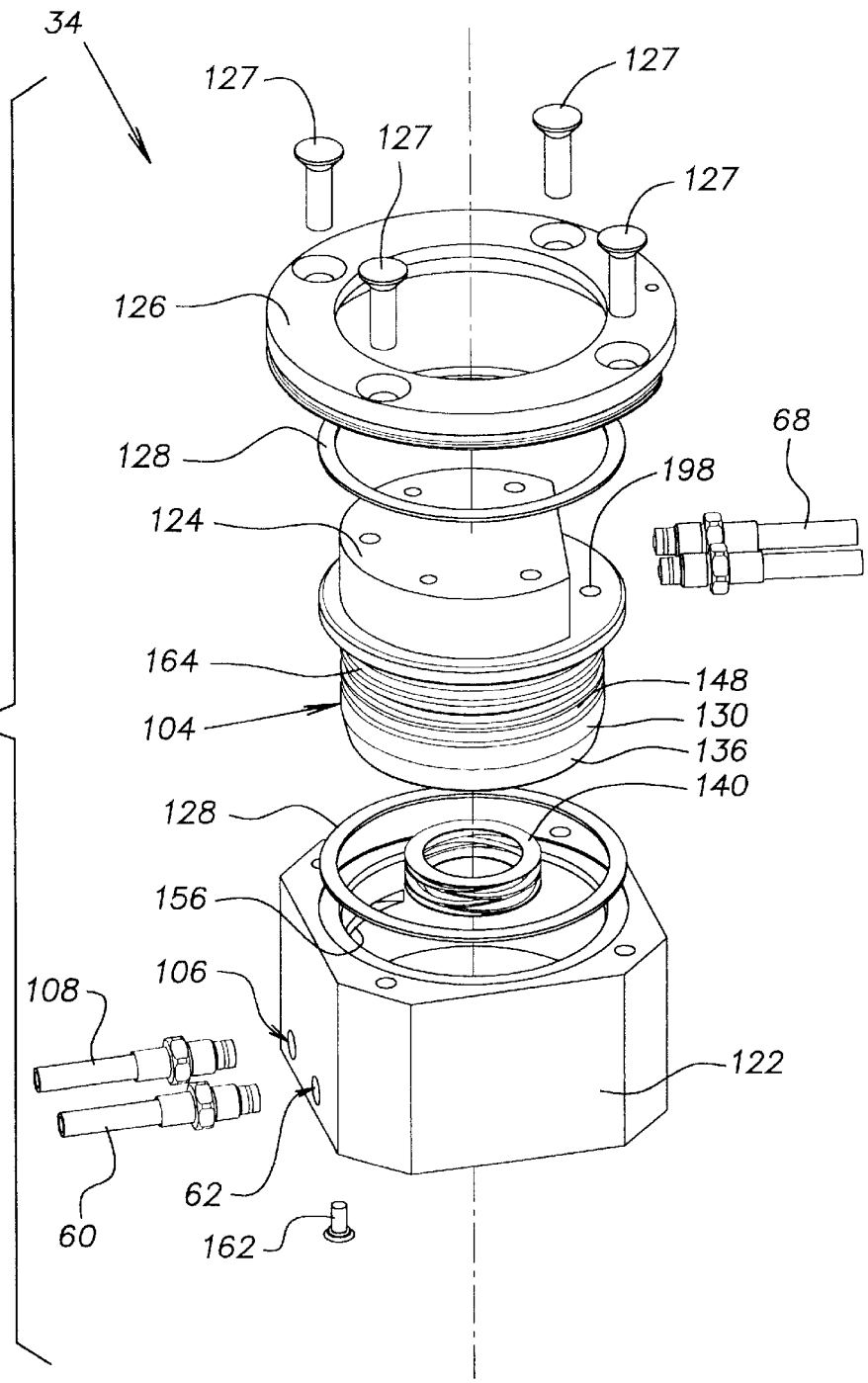
FIG. 3 is an exploded view of a rotary shoulder joint of the articulated arm of FIG. 1.
Figure 6:
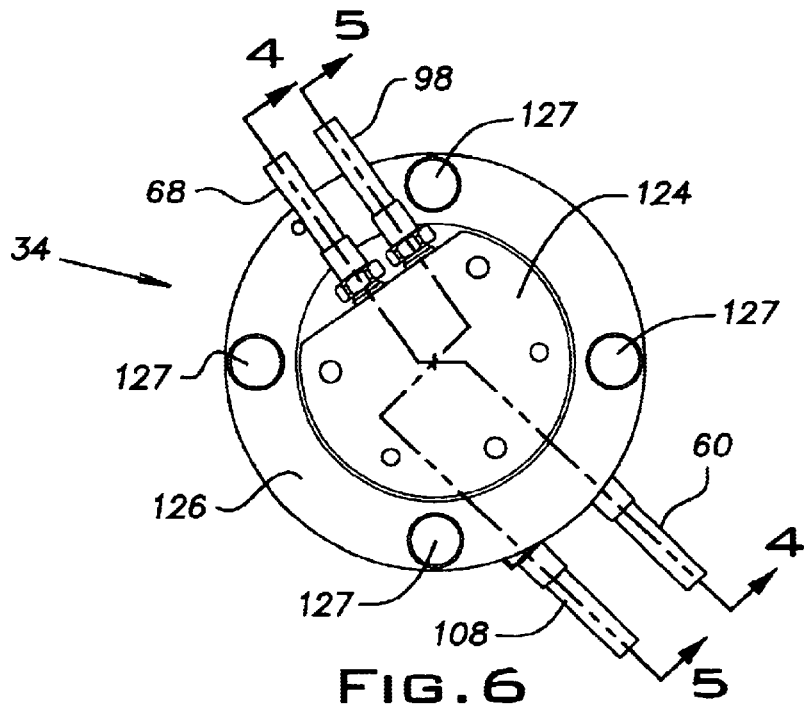
FIG. 6 is a top view of the rotary shoulder joint of FIG. 3.

As best shown in FIGS. 3–5, the friction brake assembly 104 consists of a disc brake 130 that slides freely along a shaft 132 of the face plate 124 and is prevented from rotation relative to the face plate 124 by at least one guide pin 134. The brake 130 has a frustoconical engaging surface 136 which, when forced downward, engages a complementary frustoconical surface 138 on the inside of the housing. A brake biasing spring 140 which biases the brake 130 upward and normally keeps the frustoconical surfaces 136, 138 separated. Multiple brake biasing springs (not shown) could also be used in place of the single spring 140.

By using frustoconically shaped surfaces, as opposed to traditional flat disk-shaped engaging surfaces, the braking power of the joints is significantly increased without increasing the overall size of the joints. The presently illustrated embodiment of the arm 10 is designed to hold a minimum of eight pounds of force applied at the distal end 40 while the arm is extended thirty inches in a horizontal direction. Approximately 115 psi of fluid pressure is required to provide sufficient staying power to the joints 32, 34, 36, 44. This performance is superior to many prior art devices that support only a few pounds of force.

As best shown in FIG. 4, the first fluid passage 64 terminates at one end into the first fluid inlet 62 in the housing 122 and at the other end into the first fluid outlet 66 in the face plate 124. The intermediate portion of the first fluid passage 64 is defined by a horizontal bore 142 and a vertical bore 144 through the face plate 124 and a horizontal bore 146 through the housing 122. The first fluid passage 64 is isolated from the second fluid passage 102 by a brake o-ring 148 retained by the brake 130 and two shaft o-rings 150 retained by the face plate shaft 132.

As best shown in FIG. 5, the second fluid passage 102 terminates at one end into the second fluid inlet 100 in the face plate 124 and at the other end into a second fluid outlet 106 in the housing 122. The intermediate portion of the second fluid passage 102 is defined by a horizontal bore 152 and a vertical bore 154 in the face plate 124, the space between the face plate 124 and the brake 130, and a notch 156, a vertical bore 158 and a horizontal bore 160 in housing 122. In the current embodiment, the housing 122 is machined from a solid piece of metal. Consequently, the vertical bore 158 is machined by drilling through the exterior of the housing 122, and thus a plug 162 is provided to isolate the bore 158 from the atmosphere. Alternately, the housing 122 could be cast and the bore 158 would be cast in place, thus eliminating the need for the plug 162. The second fluid passage 102 is further isolated from the atmosphere by a face plate o-ring 164 retained by the face plate 124. As previously mentioned, the second fluid passage 102 is isolated from the first fluid passage 64 by a brake o-ring 148 retained by the brake 130 and two shaft o-rings 150 retained by the face plate shaft 132.

When fluid pressure is present in the second fluid passage 102 (i.e. when an external fluid pressure source is connected to the fluid supply stem 20 and the valve 52 is in an open position), the fluid forces the brake 130 to slide downward along the shaft 132 of the face plate 124 causing the frustoconical surface 136 to engage with the complementary surface 138 of the housing 122 (see FIG. 5). As mentioned above, a frustoconical shape was chosen to enhance the holding power of the joint 34. The resulting angle of the surfaces 136, 138 amplifies the normal force.

The construction and operation of the elbow joint 36 is substantially identical to that of the shoulder joint 34.

As shown in FIGS. 8–11, the base joint 32 varies from that of the shoulder joint 34 primarily in that the second fluid outlet has been eliminated and that the first fluid inlet 54 is positioned vertically in the bottom center of a base joint housing 166 to allow for attachment of the fluid supply stem 20 to the first fluid inlet 54. As a result, the first fluid passage 56 of the base joint 32 is defined by the first fluid inlet 54 in the housing 166 and a vertical bore 168 and the fluid outlet 58 in a face plate 170. The second fluid passage 112 is defined by the second fluid inlet 110 and a vertical bore 172 in the face plate 170 and the space between the face plate 170 and a disc brake 174. Other details of the construction and operation of the base joint 32 are substantially identical to those described above with regard to the shoulder joint 34.

As shown in FIGS. 12 and 13, the ball joint 44 comprises a ball 176, a ball joint sleeve 178 and the friction brake assembly 116. The sleeve 178 is threaded onto the wrist assembly 38 and retains the ball 176 between the friction brake assembly 116 and an opening 180 in the sleeve 178. The friction brake assembly 116 comprises a brake 182 and a biasing spring 184. The brake 182 has an engaging surface 186 that is complementary to a portion of the ball 176. The biasing spring 184 pushes the brake 182 toward the ball 176 so that the engaging surface 186 and the ball 176 are always in at least minimal contact. This prevents the instrument stem 46 from moving until the surgeon 12 applies force.

When the valve 52 is open, the additional force of the fluid provided at the fluid inlet 84 against the brake assembly 116 causes the brake 182 to engage the ball 176 firmly, locking the ball joint 44. When the valve 52 is closed by the push-button 50, the fluid is discharged and the ball 176 can be moved by the surgeon by gripping and applying a moderate force to the instrument stem 46.

Figure 14:
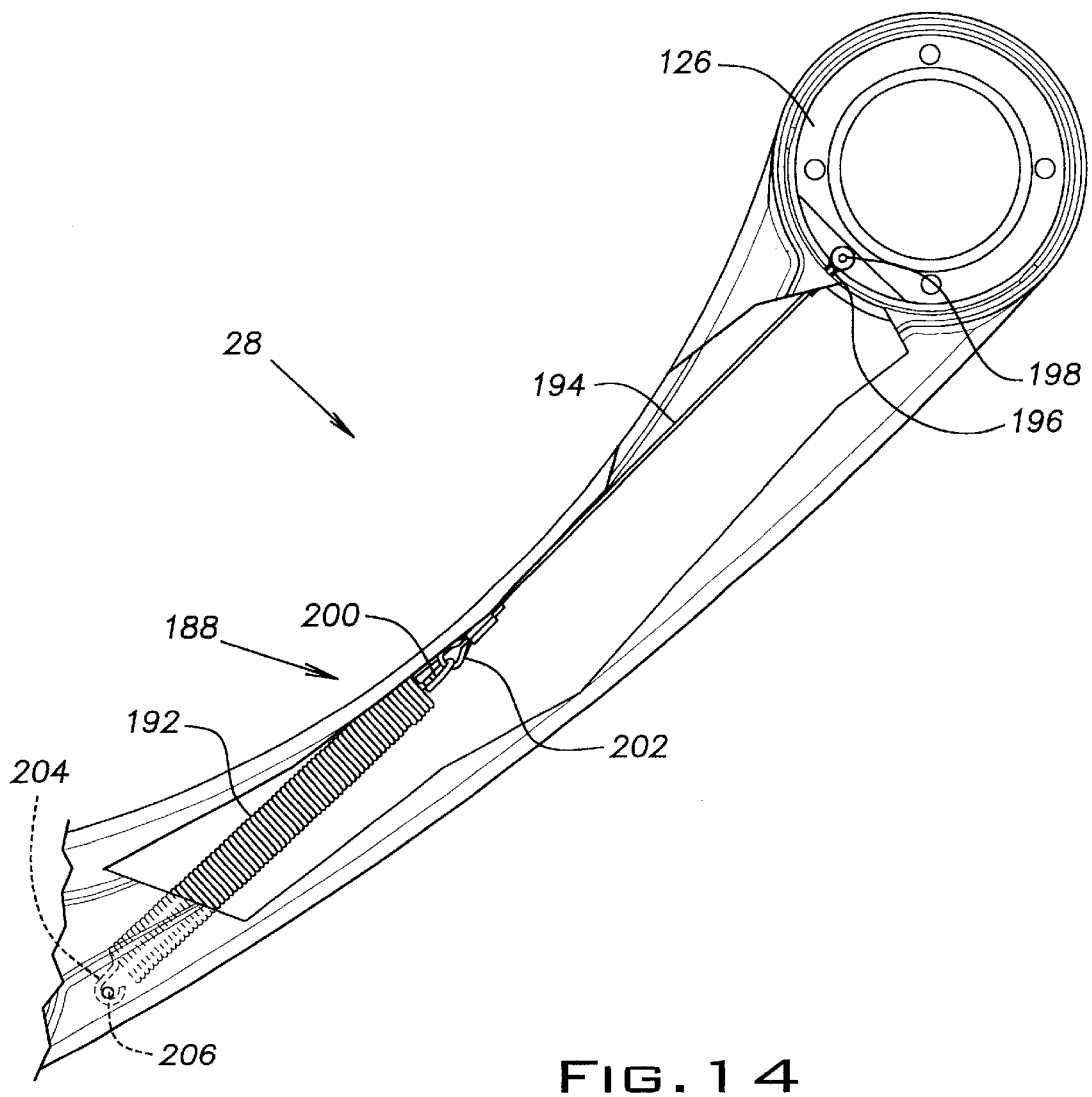
FIG. 14 is a cut-away view of a portion of the articulated arm of FIG. 1 showing a counter balance mechanism.
Figure 15:
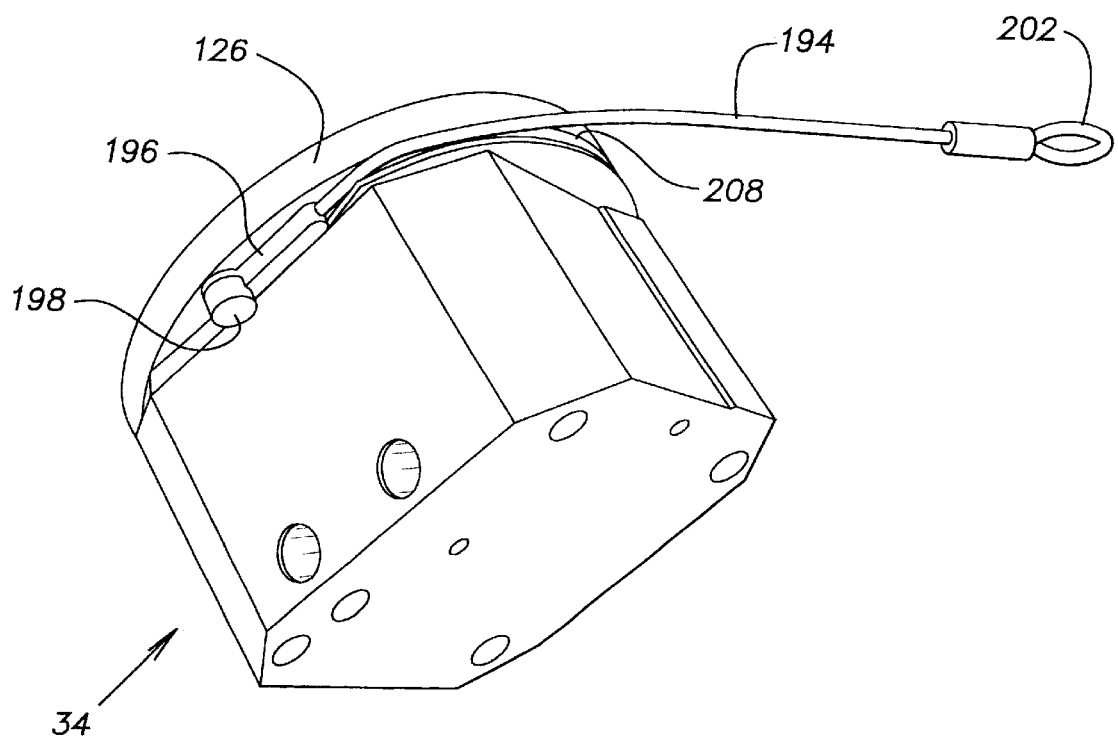
FIG. 15 is a perspective view showing a shoulder joint of the articulated arm of FIG. 1 with an attached counter balance cable.

As shown in FIGS. 14 and 15, the counter balance mechanism 188 is provided to the shoulder joint 34, in part, to prevent the weight of the upper arm 28, forearm 30 and wrist assembly 38 from inadvertently collapsing the arm onto the patient when the shoulder joint 34 is unlocked. The counter balance 188 also makes it easier for the surgeon 12 to position instruments, since it reduces the perceived weight of the arm 10. As shown in FIG. 2, a hard stop or motion-limiting mechanism 190 and a cooperating rib 191 are provided on the torso 26 and upper arm 28 respectively, to limit the range of motion of the shoulder joint 34. The base joint 32 is permitted to spin infinitely (greater than 360 degrees).

Referring again to FIGS. 14 and 15, the counter balance 188 comprises an extension spring 192 and a cable 194. A first end 196 of the cable 194 is secured to the retaining ring 126 of the shoulder joint 34 using a screw 198. A hook-shaped first end 200 of the extension spring 192 is secured to a looped second end 202 of the cable 194. A hook-shaped second end 204 of the extension spring 192 is secured to the upper arm 28 by a pin 206.

FIG. 14 is a cutaway view of the upper arm 28 with the shoulder joint 34 partially removed. Only the retaining ring 126 of the shoulder joint 34 is shown. The retaining ring is in fixed connection with the torso 26 and is rotationally associated with the upper arm 28. The position of the upper arm 28 reletive to the retaining ring 126 of the shoulder joint 34 shown in FIG. 14, such that the cable 194 is fully extended toward the spring 192, indicates that upper limit of the counter balance mechanism 188. This position represents the full extension of the upper arm 28 reletive to the torso 26. In this position the tension in the spring 192 is minimal so that it just keeps the cable 194 taut.

As best shown by both FIGS. 14 and 15, as the upper arm 28 is moved down, such that the rib 191 of the upper arm 28 approaches the stop 190, the cable 194 is wound around an annular groove 208 in the retaining ring 126. This winding of the cable 192 shortens the length of the cable 194 extending from the shoulder joint 34 and extending the spring 192. The resulting tension of the spring 192 offsets at least a portion of the weight of the upper arm 28, the forearm 30 and the wrist assembly 38. FIG. 15 shows the cable 192 partially wound around the ring 126, such that it rests within and is kept aligned by the annular groove 208.

Alternatively, the stop mechanisms and counter-balances of the above-described embodiment could be eliminated, allowing unlimited pivoting (greater than 360 degrees) of the upper arm 28 about the shoulder joint 34.

Although a particular embodiment of the invention has been described in detail, it is understood that the invention is not limited correspondingly in scope, but includes all changes and modifications coming within the spirit and terms of the claims appended hereto.

What is claimed is:

1. An articulated arm for holding surgical instruments, comprising:
    a plurality of elongated arm members;
    a plurality of rotational joints connecting said arm members end to end, such that the members are pivotable about the joints and at least one of said joints is releasably lockable by fluid pressure; and
    a plurality of tubes communicating fluid pressure between two adjacent joints;
    wherein when two adjacent members are pivoted relative to one another, the plurality of tubes connecting a particular pair of joints remains substantially stationary with respect to the arm member connecting that pair of joints.

2. The articulated arm of claim 1, further comprising a fluid pressure operated friction brake provided for locking at least one of said joints.

3. The articulated arm of claim 2, wherein the friction brake includes a substantially frustoconically shaped engaging surface.

4. The articulated arm of claim 1, wherein the fluid pressure is produced by a gas.

5. The articulated arm of claim 4, wherein the gas is selected from a group consisting of nitrogen, carbon dioxide and compressed air.

6. The articulated arm of claim 1, wherein the arm is used within a sterile field and wherein discharge of fluid for the purpose of unlocking the arm is adapted such that fluid is not directly discharged into the sterile field.

7. The articulated arm of claim 1, further comprising a check valve that prevents inadvertent unlocking of the joints in the event that a source of fluid pressure is interrupted.

8. The articulated arm of claim 1, wherein a plurality of fluid paths is provided to each joint, each of the fluid paths being isolated from the others.

9. The articulated arm of claim 1, further comprising a fluid switch located near a distal end of the arm for selectively controlling the fluid pressure within at least one of the joints, thereby unlocking the at least one joint.

10. The articulated arm of claim 9, wherein the arm includes a plurality of said rotational joints and wherein all of the plurality of joints are unlocked by operating the fluid switch.

11. The articulated arm of claim 1, wherein adjacent arm members are pivotable about at least one of said plurality of joints by greater than 360 degrees.

12. The articulated arm of claim 1, wherein a motion-limiting mechanism is provided to at least one of said plurality of joints.

13. An articulated arm for holding surgical instruments, comprising:
    first and second arm members;
    a joint connecting an end of the first member to an end of the second member, such that the members are pivotable about the joint;
    a housing provided to the joint;
    a friction brake provided to the joint for selectively locking said joint in a fixed position;
    a external source of fluid pressure;
    first and second fluid inlets provided to said joint; and
    a fluid outlet provided to said joint;
    wherein a first portion of fluid is provided by said external source to said first fluid inlet and a second portion of fluid is provided by said external source to said second fluid inlet and each are isolated from one another within said housing; and
    wherein positive pressure created by said second fluid actuates said friction brake, thereby locking said joint.

14. An articulating joint for a work-holding arm, comprising:
    a housing;
    a face plate;
    a friction brake assembly including a brake having a frustoconical engaging surface; and
    first and second fluids being isolated from one another within the housing;
    wherein said second fluid provides actuating pressure to said friction brake assembly.

15. An articulating joint for a work-holding arm, comprising:
    a housing having a first fluid inlet;
    a face plate having a second fluid inlet and a fluid outlet;
    a friction brake assembly;
    a first fluid passage communicating said first fluid inlet with said outlet; and
    a second fluid passage communicating said second fluid inlet with said friction brake assembly;
    wherein said face plate and said friction brake assembly are substantially coaxial to and positioned substantially within said housing, and wherein said first fluid passage and said second fluid passage are isolated from one another within the joint.

16. The articulating joint of claim 15, further comprising a second fluid outlet, wherein said second fluid passage communicates said second fluid inlet with said friction brake assembly and said second fluid outlet.

17. A friction brake assembly for an articulating joint for a work-holding arm, comprising:
    a rotational, fluid pressure operated brake assembly;
    at least one fluid pressure inlet;
    at least one fluid pressure outlet in fluid connection with one of said at least one fluid pressure inlet;
    wherein one of said at least one fluid inlet is operatively associated with the brake assembly and wherein one of said at least one fluid pressure inlet is rotatably disposed with respect to one of said at least one fluid pressure outlet.

* * * * *